United States Patent
Savage et al.

(10) Patent No.: US 8,067,055 B2
(45) Date of Patent: Nov. 29, 2011

(54) DRUG-DELIVERY ENDOVASCULAR STENT AND METHOD OF USE

(75) Inventors: Douglas R. Savage, Del Mar, CA (US); John E. Shulze, Rancho Santa Margarita, CA (US); Ronald E. Betts, La Jolla, CA (US); Sepehr Fariabi, Newport Coast, CA (US); Shih-Horng Su, Irvine, CA (US)

(73) Assignee: Biosensors International Group, Ltd. (BM)

( * ) Notice: Subject to any disclaimer, the term of this patent is extended or adjusted under 35 U.S.C. 154(b) by 837 days.

(21) Appl. No.: 11/690,768

(22) Filed: Mar. 23, 2007

(65) Prior Publication Data

US 2008/0097568 A1   Apr. 24, 2008

Related U.S. Application Data

(60) Provisional application No. 60/853,077, filed on Oct. 20, 2006.

(51) Int. Cl.
*A61L 33/00* (2006.01)

(52) U.S. Cl. ......... 427/2.25; 623/1; 623/1.11; 623/1.12; 427/2.24; 606/198

(58) Field of Classification Search .................. 623/1.11, 623/1, 11; 606/198; 427/2.25, 2.24
See application file for complete search history.

(56) References Cited

U.S. PATENT DOCUMENTS

| | | |
|---|---|---|
| 3,929,992 A | 12/1975 | Sehgal et al. |
| 4,316,885 A | 2/1982 | Rakhit |
| 4,650,803 A | 3/1987 | Stella et al. |
| 4,885,171 A | 12/1989 | Surendra et al. |
| 4,990,155 A | 2/1991 | Wilkoff |
| 5,100,899 A | 3/1992 | Calne |
| 5,120,842 A | 6/1992 | Failli et al. |
| 5,151,413 A | 9/1992 | Caufield et al. |
| 5,163,952 A | 11/1992 | Froix |
| 5,258,020 A | 11/1993 | Froix |
| 5,258,389 A | 11/1993 | Goulet et al. |
| 5,288,711 A | 2/1994 | Mitchell et al. |
| 5,306,286 A | 4/1994 | Stack et al. |
| 5,342,348 A | 8/1994 | Kaplan |

(Continued)

FOREIGN PATENT DOCUMENTS

EP   0 875 218 A3   11/1998

(Continued)

OTHER PUBLICATIONS

Denny, W.A. and Cain, B.F., "Potential antitumor agents. 27. Quantitative structure—antileukemic (L1210) activity relationships for the omega-[4-(9-acridinylamino)phenyl]alkanoic acids", *Journal of Medicinal Chemistry*, 21(5): 2190-2200 (1990).

(Continued)

*Primary Examiner* — Dah-Wei Yuan
*Assistant Examiner* — Andrew Bowman
(74) *Attorney, Agent, or Firm* — Kilpatrick Townsend & Stockton LLP

(57) ABSTRACT

A radially expandable, endovascular stent designed for placement at a site of vascular injury, for inhibiting restenosis at the site, a method of using, and a method of making the stent. The stent includes a radially expandable body formed of one or more metallic filaments where at least one surface of the filaments has a roughened or abraded surface. The stent may include a therapeutic agent on the abraded surface.

8 Claims, 14 Drawing Sheets

U.S. PATENT DOCUMENTS

| | | | |
|---|---|---|---|
| 5,362,718 A | 11/1994 | Skotnicki et al. | |
| 5,441,515 A | 8/1995 | Khosravi et al. | |
| 5,464,650 A | 11/1995 | Berg et al. | |
| 5,516,781 A | 5/1996 | Morris et al. | |
| 5,527,337 A | 6/1996 | Stack et al. | |
| 5,607,467 A | 3/1997 | Froix | |
| 5,609,629 A | 3/1997 | Fearnot et al. | |
| 5,649,977 A | 7/1997 | Campbell | |
| 5,665,772 A | 9/1997 | Cottens et al. | |
| 5,707,385 A | 1/1998 | Williams | |
| 5,713,949 A | 2/1998 | Jayaraman | |
| 5,716,981 A | 2/1998 | Hunter et al. | |
| 5,733,327 A | 3/1998 | Igaki et al. | |
| 5,735,872 A * | 4/1998 | Carpenter et al. | 623/1.16 |
| 5,769,884 A | 6/1998 | Solovay | |
| 5,824,048 A | 10/1998 | Tuch | |
| 5,843,172 A | 12/1998 | Yan | |
| 5,860,999 A | 1/1999 | Schnepp-Pesch et al. | |
| 5,873,904 A | 2/1999 | Ragheb et al. | |
| 5,895,407 A | 4/1999 | Jayaraman | |
| 5,902,317 A | 5/1999 | Kleshinski et al. | |
| 5,912,253 A | 6/1999 | Cottens et al. | |
| 5,922,393 A | 7/1999 | Jayaraman | |
| 5,972,027 A | 10/1999 | Johnson | |
| 6,013,853 A | 1/2000 | Athanasiou et al. | |
| 6,019,784 A | 2/2000 | Hines | |
| 6,022,371 A | 2/2000 | Killion | |
| 6,042,606 A | 3/2000 | Frantzen | |
| 6,053,939 A * | 4/2000 | Okuda et al. | 623/1.43 |
| 6,080,177 A | 6/2000 | Igaki et al. | |
| 6,096,175 A | 8/2000 | Roth | |
| 6,099,562 A | 8/2000 | Ding et al. | |
| 6,129,755 A | 10/2000 | Mathis et al. | |
| 6,153,252 A | 11/2000 | Hossainy et al. | |
| 6,156,062 A | 12/2000 | McGuinness | |
| 6,174,329 B1 | 1/2001 | Callol et al. | |
| 6,190,406 B1 | 2/2001 | Duerig et al. | |
| 6,197,013 B1 | 3/2001 | Reed et al. | |
| 6,231,600 B1 | 5/2001 | Zhong | |
| 6,248,129 B1 | 6/2001 | Froix | |
| 6,273,913 B1 | 8/2001 | Wright et al. | |
| 6,299,604 B1 | 10/2001 | Ragheb et al. | |
| 6,368,346 B1 | 4/2002 | Jadhav | |
| 6,368,658 B1 | 4/2002 | Schwarz et al. | |
| 6,384,046 B1 | 5/2002 | Schuler et al. | |
| 6,527,919 B1 | 3/2003 | Roth | |
| 6,540,777 B2 | 4/2003 | Stenzel | |
| 6,585,151 B1 | 7/2003 | Ghosh | |
| 6,585,764 B2 | 7/2003 | Wright et al. | |
| 6,607,598 B2 | 8/2003 | Schwarz et al. | |
| 6,623,521 B2 | 9/2003 | Steinke | |
| 6,641,611 B2 | 11/2003 | Jayaraman | |
| 6,663,881 B2 | 12/2003 | Kunz et al. | |
| 6,670,398 B2 | 12/2003 | Edwards et al. | |
| 6,676,701 B2 | 1/2004 | Rourke et al. | |
| 6,682,553 B1 * | 1/2004 | Webler, Jr. | 623/1.11 |
| 6,730,064 B2 | 5/2004 | Rajheb et al. | |
| 6,739,831 B2 | 5/2004 | Hsu et al. | |
| 6,743,463 B2 | 6/2004 | Weber et al. | |
| 6,746,773 B2 | 6/2004 | Llanos et al. | |
| 6,774,278 B1 | 8/2004 | Rajheb et al. | |
| 6,790,228 B2 | 9/2004 | Hossainy et al. | |
| 6,805,898 B1 * | 10/2004 | Wu et al. | 427/2.25 |
| 6,904,658 B2 | 6/2005 | Hines | |
| 6,911,100 B1 | 6/2005 | Gibbs et al. | |
| 6,913,617 B1 | 7/2005 | Reiss | |
| 6,939,376 B2 | 9/2005 | Shulze et al. | |
| 7,055,237 B2 | 6/2006 | Thomas | |
| 7,128,755 B2 | 10/2006 | Su et al. | |
| 2001/0020151 A1 | 9/2001 | Reed et al. | |
| 2001/0027340 A1 | 10/2001 | Wright et al. | |
| 2001/0029351 A1 | 10/2001 | Falotico et al. | |
| 2002/0005600 A1 | 1/2002 | Ma | |
| 2002/0038146 A1 | 3/2002 | Harry | |
| 2002/0051730 A1 | 5/2002 | Bodanr et al. | |
| 2002/0082679 A1 | 6/2002 | Sirhan et al. | |
| 2002/0098278 A1 | 7/2002 | Bates et al. | |
| 2002/0111590 A1 | 8/2002 | Davila et al. | |
| 2002/0111671 A1 | 8/2002 | Stenzel et al. | |
| 2002/0156022 A1 | 10/2002 | Edwards et al. | |
| 2003/0033007 A1 | 2/2003 | Sirhan et al. | |
| 2003/0050687 A1 | 3/2003 | Schwade et al. | |
| 2003/0050692 A1 | 3/2003 | Sirhan et al. | |
| 2003/0059454 A1 | 3/2003 | Barry et al. | |
| 2003/0068355 A1 | 4/2003 | Shanley et al. | |
| 2003/0077310 A1 | 4/2003 | Pathak et al. | |
| 2003/0083646 A1 | 5/2003 | Sirhan et al. | |
| 2003/0139801 A1 | 7/2003 | Sirhan et al. | |
| 2003/0159920 A1 | 8/2003 | Roth | |
| 2003/0225450 A1 | 12/2003 | Shulze et al. | |
| 2004/0010002 A1 | 1/2004 | Wasik et al. | |
| 2004/0024450 A1 | 2/2004 | Shulze et al. | |
| 2004/0030380 A1 | 2/2004 | Shulze et al. | |
| 2004/0073284 A1 | 4/2004 | Bates et al. | |
| 2004/0249442 A1 | 12/2004 | Fleming et al. | |
| 2005/0038505 A1 | 2/2005 | Shulze et al. | |
| 2005/0101624 A1 | 5/2005 | Betts et al. | |
| 2005/0271701 A1 | 12/2005 | Cottone et al. | |
| 2006/0036316 A1 | 2/2006 | Zeltinger et al. | |
| 2006/0069427 A1 | 3/2006 | Savage et al. | |
| 2006/0155361 A1 | 7/2006 | Schomig et al. | |
| 2006/0229711 A1 | 10/2006 | Yan et al. | |
| 2008/0051868 A1 | 2/2008 | Cottone et al. | |
| 2008/0051873 A1 | 2/2008 | Cottone et al. | |
| 2008/0051874 A1 | 2/2008 | Cottone et al. | |
| 2008/0051875 A1 | 2/2008 | Cottone et al. | |
| 2008/0097575 A1 | 4/2008 | Cottone | |

FOREIGN PATENT DOCUMENTS

| | | |
|---|---|---|
| EP | 0 950 386 A2 | 10/1999 |
| EP | 0 970 711 A2 | 1/2000 |
| JP | 10192413 | 7/1998 |
| WO | WO 97/35575 | 10/1997 |
| WO | WO 98/36784 A1 | 8/1998 |
| WO | WO 99/07308 | 2/1999 |
| WO | WO 01/14387 A1 | 3/2001 |
| WO | WO 01/45763 A1 | 6/2001 |
| WO | WO 02/26162 A1 | 4/2002 |
| WO | WO 02/26281 A1 | 4/2002 |
| WO | WO 02/32347 A1 | 4/2002 |
| WO | WO 02/056790 A2 | 7/2002 |
| WO | WO 03/026718 A1 | 4/2003 |
| WO | WO 2006/020742 A2 | 2/2006 |

OTHER PUBLICATIONS

Dibra, A. et al., "Influence of Stent Surface Topography on the Outcomes of Patents Undergoing Coronary Stenting: A Randomized Double-Blind Controlled Trial", *Catherization and Cardiovascular Interventions*, 65:374-380 (2005).

Ichihashi, T. et al. , "A quantitative concept of the mechanism of intestinal lymphatic transfer of lipophilic molecules", *Pharmaceutical Research*, 11(4):508-512 (1994).

Schwartz et al., "Restenosis After Balloon Angioplasty—A Practical Proliferative Model in Porcine Coronary Arteries", *Circulation*, 82(6):2190-2200 (1990).

Su, S-H. et al., "Expandable Bioresorbable Endovascular Stent. I. Fabrication and Properties", Annals of Biomedical Engineering, 31:667-677 (2003).

The International Search Report PCT application No. PCT/US2007/022284, search report dated Apr. 23, 2008, 4 pages (2008).

\* cited by examiner

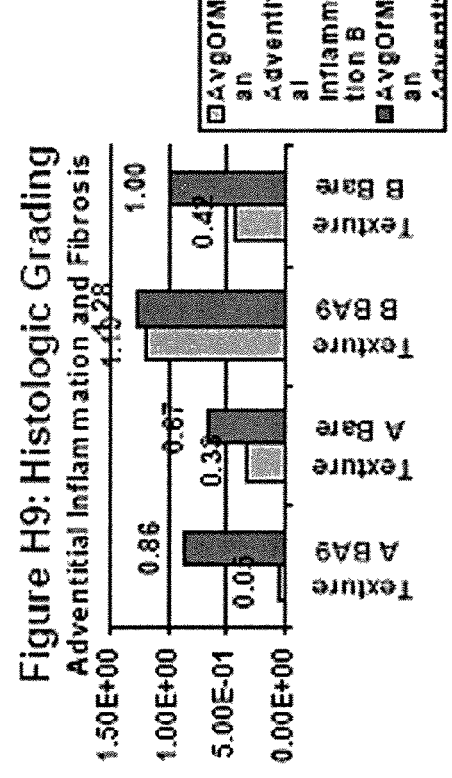
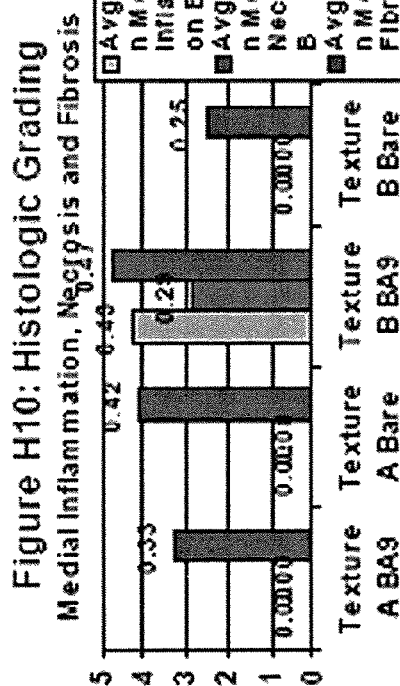
Figures 10J-K

DRUG-DELIVERY ENDOVASCULAR STENT AND METHOD OF USE

This application claims the benefit of priority to U.S. Provisional Application No. 60/853,077, filed Oct. 20, 2006.

BACKGROUND

Complications such as restenosis are a recurring problem in patients who have received artherosclerosis therapy in the form of medical procedures such as percutaneous transluminal coronary angioplasty (PTCA). Restenosis is commonly treated by a procedure known as stenting, where a medical device is surgically implanted in the affected artery to prevent it from occluding post procedure.

A stent is typically cylindrical in shape and is usually made from a biocompatible metal, such as titanium or surgical steel. Most stents are collapsible and are delivered to the occluded artery via transluminal catheter. The stent is affixed to the catheter and can be either self expanding or expanded by inflation of a balloon inside the stent that is then removed with the catheter once the device is in place. Examples of common types of stents are disclosed in US Patent Application Publication No. U.S. Pat. No. 6,936,066 to Palmaz entitled "Complaint Implantable Medical Devices and Methods of Making Same."

Complications that arise from stent therapy are restenosis and thrombosis. In an effort to overcome these complications, stents are routinely developed to have the additional feature of controlled drug elution. To accomplish this, a metal stent is coated with an API mixed with polymer, as disclosed in U.S. Pat. No. 5,716,981 issued to Hunter entitled anti-angiogenic Compositions and Methods of Use. Examples of typical therapies that are delivered in this manner are antiproliferatives, anticoagulants, anti-inflammatory agents and immunosuppressive agents, though there are many other chemical and biological agents that can be used. A porous layer of biodegradable material is often applied over the coating layer to regulate controlled release of the drug into the body. Common types of polymer coated drug eluting stents are disclosed by U.S. Pat. Nos. 6,774,278 and 6,730,064 issued to Ragheb entitled "Coated Implantable Medical Device."

It has been postulated that the presence of this polymer contributes to thrombosis due to delamination. It is thought that over time, the protective polymer may separate from the bare metal or substrate, resulting in sharp peaks or edges that come in direct contact with red blood cells, the result of which is thrombosis, causing serious illness or death in the patient. Stents have been designed that do not include a permanent polymer, like BSI biodegradable PLLA. Some stent designs have moved towards the polymerless altogether such as surface textured stents or biocompatible oil coatings.

To increase the drug loading capacity, stents can be engineered to have roughened surfaces. Rough surfaces on the stent provide for peaks and valleys which increase the total surface area of the stent thereby increasing the amount of API that may be associated with the stent. Roughening of the surface of a stent is accomplished in a number of ways, such as sintering, as disclosed in U.S. Pat. No. 5,843,172 issued to Yan entitled "Porous Medical Stent." Surface roughness is also achieved by abrasive techniques such as sandblasting and reductive acid etching as disclosed in European patent No. 0806212 issued to Leitao entitled "Device For Incorporation and Release of Biologically Active Agents." Roughening of a stent surface can also be achieved pressing indentations directly onto the device as disclosed in U.S. Pat. No. 7,055,237 Issued to Thomas entitled "Method of Forming a Drug Eluting Stent" or using the common metal working techniques of shot peening or laser peening. A stent having a mechanical anchoring layer is described in co-owned U.S. Publication No. 2006/0069427. However, the stent and catheter crossing profile serve as physical limitations for the thickness of coatings. A problem encountered with rough stents is that the crossing profile of the stent and catheter must be limited to a thickness that is narrow enough to pass through an occluded artery.

In light of the complications associated with stent therapy, it would be desirable to develop a stent that will have the increased surface area of a rough stent which can be manufactured in such a way as to maximize structural integrity and drug loading capacity. Further, it would be desirable to develop a polymerless stent that is capable of delivering API to decrease or eliminate the risk the risk of late stent thrombosis. Finally, it is desirable to develop a stent that maximizes drug loading capacity while at the same time minimizing the total thickness of the stent-catheter crossing profile.

SUMMARY

The present embodiments solve one or more of the foregoing problems by providing a medical device such as a stent and method by which a drug eluting stent is treated that will decrease the crossing profile thickness without compromising structural integrity. The disclosed embodiments also maximize drug loading capacity and/or increase fatigue resistance.

In one aspect, a nonpolymeric therapeutic agent eluting stent is provided. Preferably, the stent includes at least a portion of at least one surface having a textured or abraded microstructure. In a preferred embodiment, the therapeutic agent is applied to at least the textured portion of the stent surface.

In another aspect, methods for preparing a stent with at least one "roughened" surface are disclosed. In one embodiment, the method includes crimping a bare metal stent into a hydrocarbon film layer which creates a mask for at least one of the inner layer and sides of the stent. The outer surface is then treated with an abrasive, and the masking layer is subsequently dissolved or otherwise removed. Preferably, the stent is then sonicated, cleaned and passivated according to ASTM standards.

In another embodiment, the stent surface is treated by the process of peening. The untreated stent is clamped on to a mandrel and roughening is achieved by pressing metal particles called shot onto the stent surface using plates or rollers. Roughness may also be achieved by blasting shot at the stent surface such as by jet blasting. In another embodiment, surface roughness can also be accomplished in a similar manner that employs a laser rather than shot.

In yet another embodiment, the stent is treated by pneumatic or hydraulic press to produce the roughened surface. The untreated stent is affixed to a mandrel and a pattern is stamped onto its surface by a pneumatic or hydraulic press. In one embodiment, the pattern is predetermined. In another embodiment, the pneumatic or hydraulic press is computer controlled. An advantage of the press method is its ability to disrupt microcrystalline structures in the stent body to increase the stent body's fatigue resistance.

In another embodiment, the entire length of the stent, for example 2.5 M, is treated before it is cut into the desired stent lengths. The entire stent length is attached to a mandrel and then treated via one of the methods disclosed.

In still a further embodiment, a stent is coated with an active pharmaceutical ingredient (API) or an API and polymer combination. The coating may be achieved via spraying the desired drug or drug/polymer combination directly on to the stent surface. Further, coating the stent with the desired chemical may be achieved by dipping the stent into a solution of the desired API coating. In yet another embodiment, the stent is coated with an API or API/polymer combination abluminally by automated pipetting.

These and other aspects and embodiments of the present invention will become better apparent in view of the detailed description in conjunction with the accompanying drawings.

BRIEF DESCRIPTION OF THE DRAWINGS

The present invention will become more fully understood from the detailed description and the accompanying drawings wherein:

FIGS. 10A-10K are graphs of the histomorphometry of the microstructure stent.

DETAILED DESCRIPTION

I. Endovascular Stent

Figure 1:
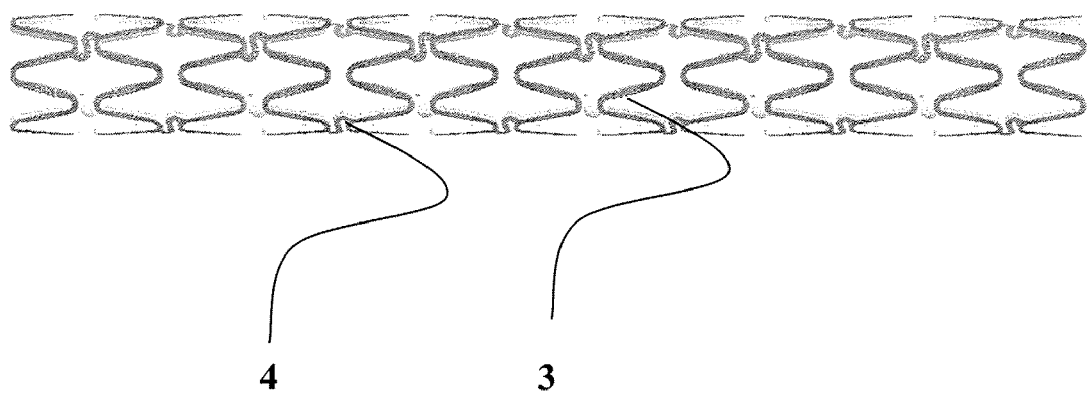
FIG. 1 is a scanned image of an endovascular stent having a metal filament body.

FIG. 1 shows a stent constructed in accordance with the invention, in the stent's contracted state. The stent includes a structural member or body with at least one surface being at least partly roughened or abraded at least for holding and releasing an anti-restenosis compound, as will be described further below.

In the embodiment shown, the stent body is formed of a series of tubular members called struts 3 connected to each other by filaments called linkers 4. Each strut 3 has an expandable zig-zag, sawtooth, helical ribbon coil or sinusoidal wave structure, and the connections to each linker 4 serve to increase overall stent flexibility. The contracted-state diameter of the stent is between approximately 0.5 mm-2.0 mm, preferably 0.71 to 1.65 mm, and a length of between 5-100 mm. The expanded stent diameter is at least twice and up to 8-9 times that of the stent in its contracted state, for example, a stent with a contracted diameter of between 0.7 to 1.5 mm may expand radially to a selected expanded state of between 2.0-8.0 mm or more. Stents having this general stent-body architecture of linked, expandable tubular members are known, for example, as described in PCT Publication No. WO 99/07308, which is commonly owned with the present application and expressly incorporated by reference herein.

Preferably, the stent structure is made of a biocompatible material, such as stainless steel. Further examples of biocompatible materials that are typically used for the stent structure are, tantalum, titanium, nitinol, gold, platinum, inconel, iridium, silver, tungsten, or another biocompatible metal, or alloys of any of these; carbon or carbon fiber; cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or another biocompatible polymeric material, or mixtures or copolymers of these; poly-L-lactic acid, polyglycolic acid or copolymers thereof, a polyanhydride, polycaprolactone, polyhydroxybutyrate valerate or another biodegradable polymer, or mixtures or copolymers of these; a protein, an extracellular matrix component, collagen, fibrin or another biologic agent; or a suitable mixture of any of these. An example of a typical stent is described in U.S. Pat. No. 6,730,064. The dimensions of each stent will vary depending on the body lumen in which they are to be delivered. For example, a stent may have a diameter ranging from approximately 0.5 mm to approximately 25.0 mm and a length that ranges from approximately 4 mm to approximately 100 mm or longer. An example of stent measurements is described in U.S. Pat. No. 6,939,376 to Shulze, which is commonly owned and expressly incorporated by reference herein.

Figure 2A:
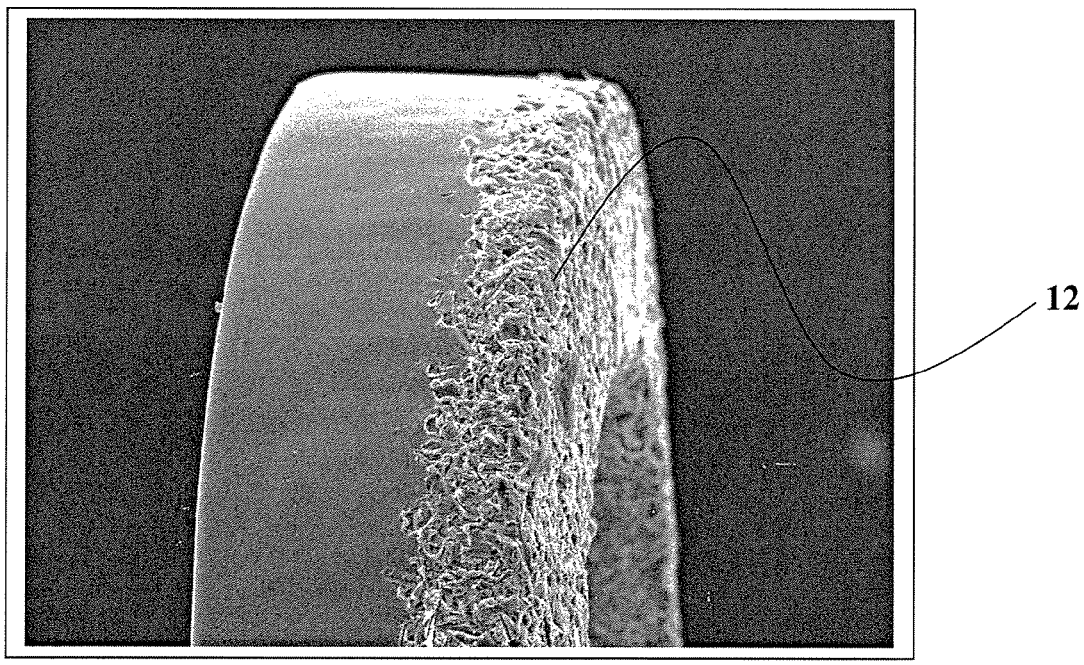
FIG. 2A is a scanning electron micrograph of an abraded stent surface.
Figure 2B:
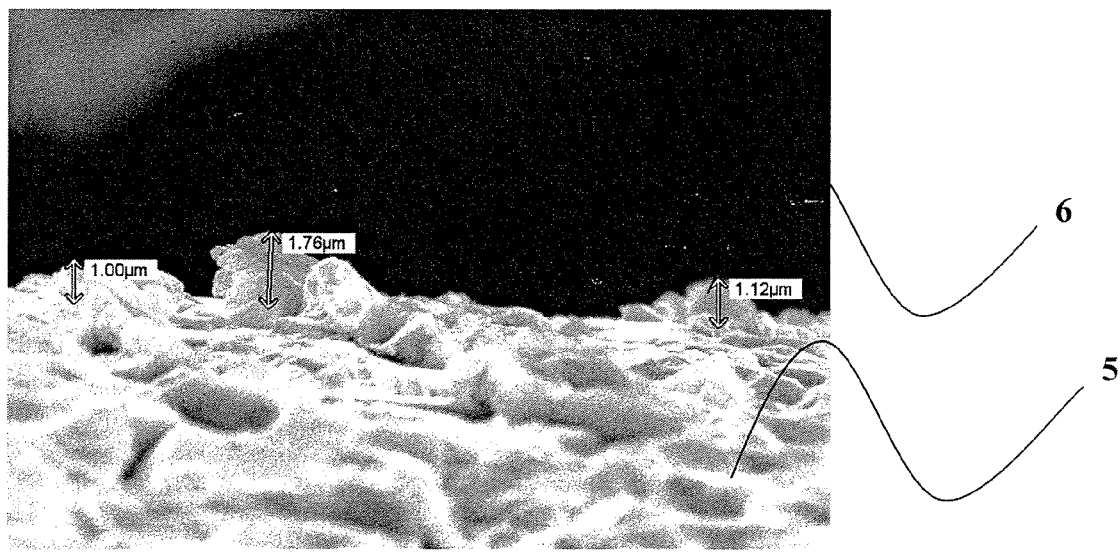
FIG. 2B is a scanning electron micrograph of the surface of FIG. 2A showing quantification of peaks generated on the stent surface after abrasion.
Figure 2C:
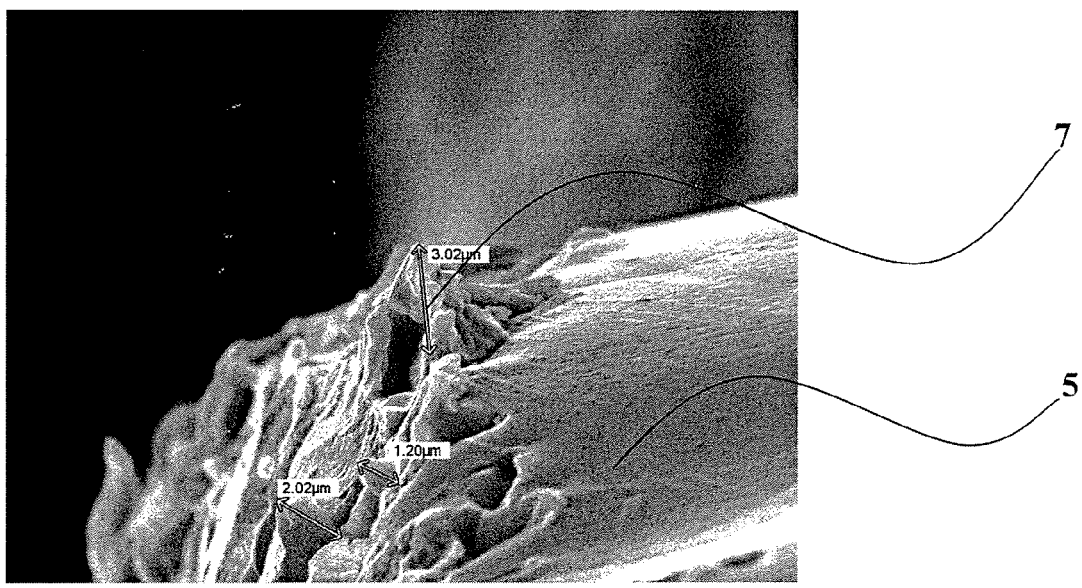
FIG. 2C is a scanning electron micrograph of the surface of FIG. 2A showing quantification of valleys generated on the stent surface after abrasion.
Figure 3A:
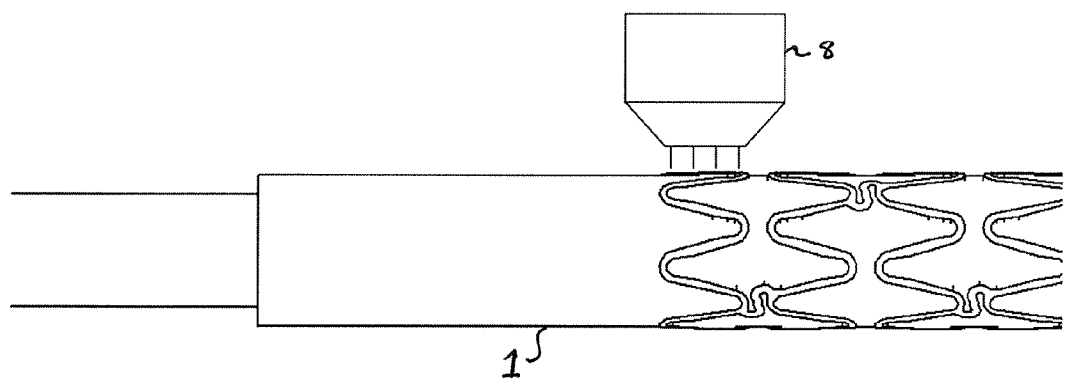
FIG. 3A is an illustration of a pneumatic press treating a stent surface.
Figure 3B:
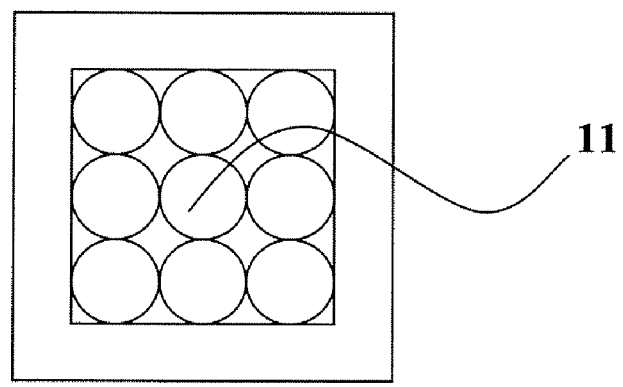
FIG. 3B is a close up frontal view of the fixed-head punch assembly of FIG. 3A showing the pneumatic press with multiple peeners.
Figure 3C:
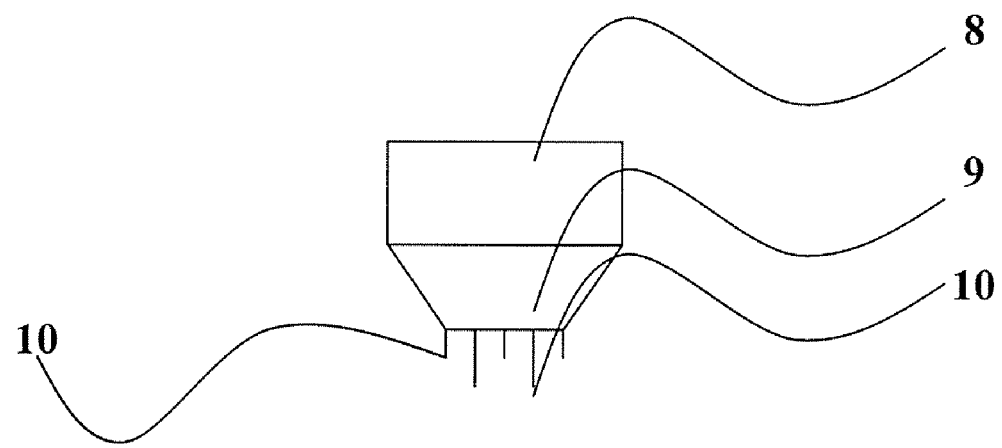
FIG. 3C is close up side view of the fixed head punch assembly of FIG. 3B.
Figure 3D:
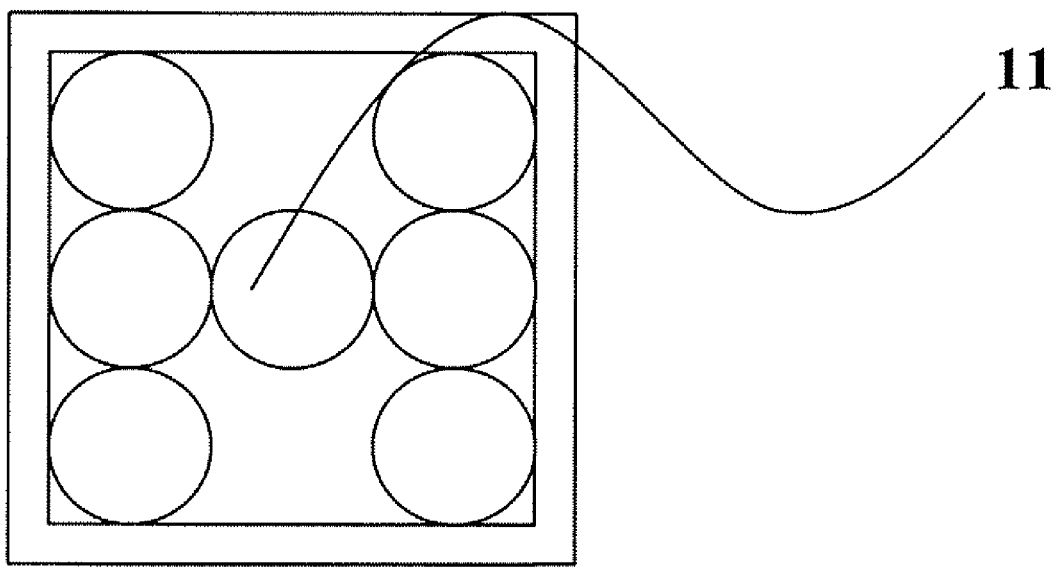
FIG. 3D is a close up frontal of the fixed-head attachment for the punch assembly of the pneumatic press of FIG. 3A showing an exemplary pattern.

As seen in FIG. 2A, at least a portion of at least one of the surfaces of the stent has a roughened or abraded microstructure or textured surface. This microstructure can include at least one therapeutic agent that elutes from the microstructure. As seen in FIGS. 2B-2C, the roughened or textured surface provides interstices or vertically projecting surface features and/or regions of undercuts or recesses. It will be appreciated that a solution of or containing a therapeutic agent can be drawn, e.g., by capillary forces into such recesses and coat the projecting surfaces. In this manner, the surface area for coating the stent may be increased. The thickness of such layer refers to the average thickness of the layer, e.g., average depth of the infusible portion of the layer.

Preferably, and as seen in FIG. 2A, at least a portion of the abluminal surface of the stent includes the microstructure surfacing.

II. Methods of Preparing Textured Surface

In one embodiment, the method includes use of a mask to prevent at least a portion of the stent from being abraded. Preferably, the mask is a hydrocarbon film, such as PARA-FILM®, however, it will be appreciated that any suitable barrier to abrasion is suitable for use in these methods. Accordingly, in a preferred embodiment, at least the luminal surface of the stent is not abraded. In one embodiment, a sheet of the mask approximately 5 mm by 60 mm is rolled around the diameter of a mandrel such as a 1.4 mm glass capillary tube. The stent is positioned onto the mandrel and hand-crimped into the hydrocarbon mask. A stereo microscope set between 10× and 40× may be used to ensure that the portion of the stent that is not to be abraded is covered by the mask. In a preferred embodiment, at least 80% of the stent wall thickness on all surfaces is masked by the hydrocarbon film layer.

In one embodiment, the stent surface 5 is then treated by utilizing microblasting systems, such as the MICRO BLASTER® and PROCENTER® by Comco, Inc. or an equivalent. In one embodiment, 25 µm of an abrasive, such as aluminum oxide, is used to roughen the stent surface 5. The pressure is adjusted to 40 psi±5 psi, and a spray nozzle is positioned approximately 2.5 cm to 5.0 cm from the stent surface 5, making multiple passes over the stent.

In another embodiment, the mask is removed by any appropriate means such as via ultrasonic cleaning. Typically the ultrasonic cleaner is filled with deionized water which is heated to 45° C. A sample vial of HPLC grade chloroform is heated to between 50-60° C. on a hotplate. A glass capillary tube mandrel with a treated stent is incubated in a vial of 40° C. and 50° C. HPLC grade chloroform for 5-10 minutes. The vial containing the chloroform and mandrel is then soniciated in 45° C. deionized water for two minutes.

Due to the roughening of the stent surface 5, different elements are expressed on the metal surface, which can increase the susceptibility to corrosion. As a result, the treated stent is generally passivated according to ASTM standards and cleaned in a series of solvents such as Chloroform, Acetone and/or Isopropyl Alcohol. In one embodiment, after the mask is removed and the treated stent is sonicated, it is removed from the vial of chloroform. A sample vial is rinsed with Acetone and then refilled with Acetone. The treated stent is placed in the vial and sonicated in the ultrasonic cleaner for two minutes. The vial is rinsed with isopropyl alcohol and then refilled with isopropyl alcohol. The stent is sonicated in the ultrasonic cleaner for two more minutes. The treated stent is then passivated in a 60° C.±3° C. 20% by volume Nitric Acid bath for 30 minutes. The stent is then rinsed 10 times with copious amounts of deionized water. The stent is then placed in 600 mL of a solvent such as isopropyl alcohol and sonicated in the ultrasonic cleaner for 5 minutes and allowed to air dry.

In another embodiment, the surface of the stent is uniformly abraded in a controlled manner via shot peening. Roughening of a stent surface 5 is accomplished using metal particles called shot that range in size from approximately 1 to 5 microns and is made from an atomic element having at least a weight of 43 g/mol. For example, the shot may be in the form of particulate tantalum, particulate tungsten, particulate platinum, particulate iridium, particulate gold, particulate bismuth, particulate barium, particulate zirconium and alloys thereof. Examples of suitable alloys include a platinum/nickel alloy and a platinum/iridium alloy.

The stent surface 5 may be treated by placing desired amount of shot over a predetermined portion of the stent surface 5 and in the desired pattern. Pressure is applied to the particles using plates or rollers to make indentations in the stent surface 5. Roughness can also be achieved by jet blasting the particles at the stent surface 5 at a velocity sufficient to make indentations. An example of shot peening a metal surface is described in U.S. Pat. No. 6,911,100.

In a further embodiment, this uniform, controlled surface roughness can also be achieved similar to above by employing a laser rather than the use of shot. A series of electric discharges are applied to the desired portion of the outer or inner stent surface 5. The electric discharges contact the surface with sufficient energy to vaporize the material on the surface of the stent, creating pits, sometimes called voids, the combined effect of which is a rough surface having increased surface area. An example of this process is described in U.S. Pat. No. 6,913,617.

In another embodiment, the surface of the stent is uniformly treated by compression. The stent is affixed to a mandrel, which is inserted into a die that is equipped with preformed raised portions that form indentations in the desired amount, shape, size and pattern on the stent surface 5. The indentations may be made in a number of ways such as welding them onto the stent surface 5 or sandblasting. The die is then closed around the stent forming indentations of the desired depth and covering the desired surface area. The stent is treated over its entire surface, or a portion of the surface, depending on the manufacture of the die. An example of this process is described in U.S. Pat. No. 7,055,237.

In another embodiment, a stent surface 5 is treated with a pneumatic press or hydraulic press. Pneumatic presses are well known in the art as described in U.S. Pat. No. 4,079,617. Hydraulic presses are also well-known in the art as described in U.S. Pat. No. 7,033,155. As seen in FIGS. 3A-3D, the stent is positioned on a mandrel 1 that is either stationary or rotating. A computer controlled pneumatic or hydraulic press 8 is configured to treat the surface of the stent in one of several predetermined ways, for example, randomly or in a desired pattern. The punch assembly 9 of the press may be configured to contain one or more peeners 10, 11 here defined as indentation creating mechanisms. In a preferred embodiment, the punch assembly contains a plurality of peeners. It will be appreciated that the peeners may be of uniform or varied length in order to form the surface microstructure. Each peener 10, 11 remains in a retracted position until the computer is programmed to treat the stent surface 5. According to the selected program, the peeners 10, 11 will be depressed onto the stent surface 5 with enough force to result in an indentation. Generally, the punch assembly 9 is configured to be no more than width of the desired stent, for example if the stent strut 3 is 15 micron, the plurality of peeners 10, 11, will total no more than 15 micron on width as well. The number of peeners 10, 11 on a given punch assembly 9 will vary depending on the width of the stent. Similarly, the punch assembly 9 may be configured to be a preformed head affixed to the press the heads are interchangeable depending on which pattern is desired. Also, the head can be stationary and the stent is turned or in the alternative, the head can be moveable, this is embodied in a single peener 10, 11 affixed to the press that will randomly make impressions on the stent surface 5.

In another embodiment, the entire length of the stent, for example, approximately 2.5 m, is treated prior to laser cutting it into a plurality of desired stent lengths. The stent is horizontally or vertically attached to one or more mandrels 1 and abraded using one of the methods disclosed in this application. In terms of the abrading techniques, the stent is treated randomly, uniformly or in a desired pattern. Further, the length and sides of the stent is treated lengthwise, vertically or spirally. Moreover, the stent surface 5 is treated either by moving it over a stationary roughening mechanism, or in the alternative, the entire stent tube length is stationary and the roughening mechanism may be moved over the length of the tube in one of the manners disclosed, for example horizontally, vertically, spirally.

Potentiodynamic corrosion testing was performed on the treated stent to confirm the desirability of the passivation step and its effectiveness. The data shows that the treated, passivated stent breakdown potential is well within ASTM specified voltage levels standards. Therefore, after the roughening process and passivation, the treated stent does not exhibit a greater likelihood of corrosion when compared to the untreated control stent, and the roughening process does not increase the potential for restenosis and thrombosis.

The approximate thickness of an untreated stent wall is generally around 0.05 mm. As seen in FIGS. 2B-2C, the treatment of the stent surface 5 in the manner disclosed results in a treated stent surface with an average peak 6 height of approximately 1.30 μm and an average valley 7 depth of 2.08 μm. To measure the effects, if any, that the roughening process has on the stent's structural integrity, axial fatigue testing and auger analysis was performed on a treated stent. Axial fatigue testing was focused at the portion of the stent that is the most susceptible to breakage, which is the link 4 between stent struts 3. After over 3 million cycles in simulated physiological conditions, the untreated stent control and the roughed stent both remained intact. Since a portion of the treated stent is removed in the roughening process, and the treated stent is able to withstand the same conditions an untreated intact stent with more surface area is able to withstand, it is understood that the roughening process actually increases the fatigue resistance of the stent due to the disrupted microcrystalline structures of the stent body. Finally, auger analysis was performed on the treated stent to characterize the surface chemistry, which revealed similar rations of identical elements in the passivated untreated stent and the passivated treated stent. This demonstrates that the process of passivating the untreated control stent in the manner disclosed has no deleterious effects on the surface chemistry of the stent.

Preferably, an API such as the antiproliferative Biolimus A9® is applied at least to the abluminal portion of the stent. The API may be applied to the stent surface by any appropriate means including by spraying the treated surface of the stent with a solution of the API. The API solution may also be applied by dipping the entire stent into the desired API or by applying it directly to the stent surface 5 manually. Biolimus A9® has an amorphous to semi-crystalline structure that does not crack or fracture like some other crystalline limus compounds. Therefore, the properties of Biolimus A9® permit adhesion to the stent's roughened treated surface in the unexpanded state and the expanded state.

Preferably, the API material is applied to the abluminal portion of the stent via autopipetting as described in co-owned U.S. Pat. No. 6,939,376. A solution ranging in a concentration of approximately 25 mg/ml to approximately 100 mg/ml is made by dissolving the desired API in an appropriate solvent, such as ethyl acetate. The solution is placed in a reservoir with a pump designed to deliver the solution at a predetermined rate. The pump is controlled by a microcontroller, such as the 4-Axis Dispensing Robot Model available from I&J Fisnar Inc. A solution delivery tube for delivery of the solvent mixture to the stent surface 5 is attached to the bottom of the reservoir. The reservoir and delivery tube are mounted to a moveable support that moves the solvent delivery tube continuously or in small steps, for example, 0.2 mm per step along the longitudinal axis of the stent.

An uncoated stent is gripped by a rotating chuck contacting the inner surface of the stent at least one end. Axial rotation of the stent is accomplished by rotating the stent continuously, or in small degree steps, such as 0.5 degree per step. Alternatively, the delivery tube is held at a fixed position and, in addition to the rotation movement, the stent is moved along its longitudinal direction to accomplish the coating process.

The tubes are further drawn under a Bunsen burner for precise application of the drug/solvent mixture, which can vary over the length and sides of the stent as needed. It is within the scope of the invention to use more than one of the fluid dispensing tube types working in concert to form the coating, or alternately to use more than one moveable solution reservoir equipped with different tips, or containing different viscosity solutions or different chemical makeup of the multiple solutions in the same process to form the coating.

In another embodiment, a non-porous layer of parylene, parylene derivative, or another biocompatible polymer is applied to the treated stent surface, and the desired API is layered onto that. Optionally, an additional layer of slightly non-porous polymer is applied directly over the API, which aids in controlled release over time. According to the present invention, the stent comprises at least one layer of an API posited on its surface, and the other surfaces will either contain no API or one or more different APIs. In this manner, one or more APIs may be delivered to the blood stream from the lumen surface of the stent, and different treatments for different conditions are delivered on the vascular injury site surface of the stent.

Figure 4:
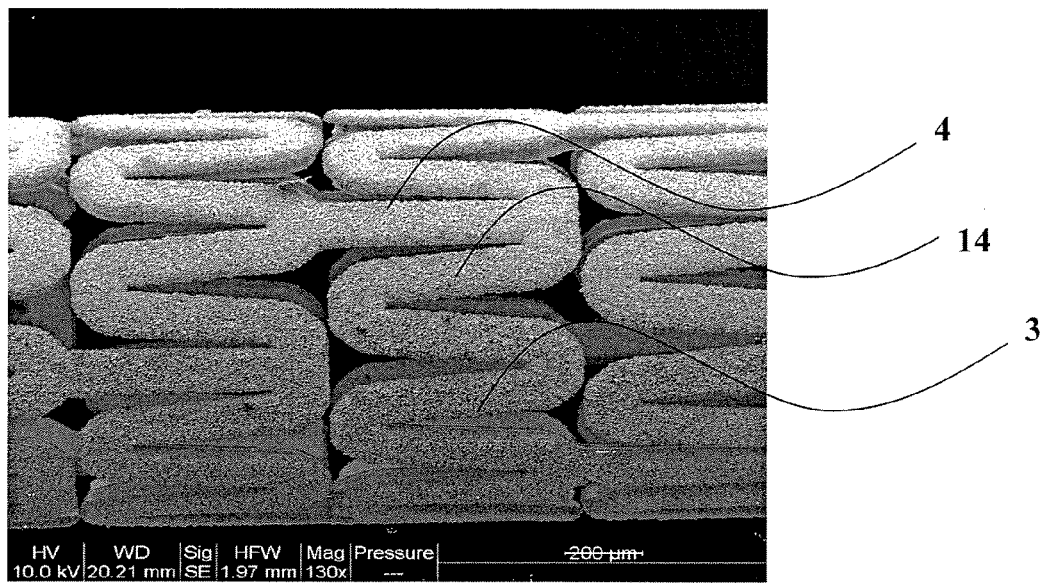
FIG. 4 is a scanning electron micrograph of a drug-coated, treated stent.

In another embodiment the stent is capable of being coated with an API molecule without the need of a polymer. As seen in FIG. 4, the process of roughening all or a portion of the stent in one of the methods disclosed above allows for the API to adhere directly to the surface of the treated stent 14. In some embodiments, the API is drawn into the valleys and cavities of the roughened surface. API molecules that are typically applied to the treated stent are antiplatelet or antithrombotic agents, or dexamethasone, dexamethasone acetate, dexamethasone sodium phosphate, or another dexamethasone derivative or anti-inflammatory steroid. The stent can also be used to deliver other types of API molecules such as thrombolytics, vasodilators, antihypertensive agents, antimicrobials or antibiotics, antimitotics, antiproliferatives, antisecretory agents, non-steroidal anti-inflammatory drugs, immunosuppressive agents, growth factors and growth factor antagonists, antitumor and/or chemotherapeutic agents, antipolymerases, antiviral agents, photodynamic therapy agents, antibody targeted therapy agents, prodrugs, sex hormones, free radical scavengers, antioxidants, biologic agents, radiotherapeutic agents, radiopaque agents and radiolabelled agents.

A variety of anti-restenosis compounds may be employed in the present embodiment, including anti-proliferative agents, such as taxol (paclitaxel), antisense compounds, doxorubicin, and most particularly, macrocyclic triene immunosuppressive compounds having the general structure indicated below, and also referred to generally as "limus" compounds. Some of the latter class of compounds, and their synthesis, are described, for example in U.S. Pat. Nos. 4,650,803, 5,288,711, 5,516,781, 5,665,772 and 6,153,252, in PCT Publication No. WO 97/35575, in U.S. Pat. No. 6,273,913B1, and in U.S. Patent Application Nos. 60/176086, 2000/021217A1, and 2001/002935A1.

The stent may be included in an assembly consisting of a stent body surrounding a deflated balloon affixed to a catheter is used to deploy the stent to the vascular injury site. The stent is introduced into the cardiovascular system of a patient via the brachial or femoral artery. The catheter assembly is advanced through the coronary vasculature until the deflated balloon and stent combination is positioned across the vascular injury site. The balloon is then inflated to a predetermined size to expand the stent to a diameter large enough to be in continuous contact with the lumen. The balloon is then deflated to a smaller profile to allow the catheter to be withdrawn from the patient's vasculature, leaving the stent in place. An example of a typical stent implantation procedure is described in U.S. Pat. No. 6,913,617.

III. Methods of Use

This section describes vascular treatment methods in accordance with the invention, and the performance characteristics of stents constructed in accordance with the invention.

The methods of the invention are designed to minimize the risk and/or extent of restenosis in a patient who has received localized vascular injury, or who is at risk of vascular occlusion. Typically the vascular injury is produced during an angiographic procedure to open a partially occluded vessel, such as a coronary or peripheral vascular artery. In the angiographic procedure, a balloon catheter is placed at the occlusion site, and a distal-end balloon is inflated and deflated one or more times to force the occluded vessel open. This vessel expansion, particularly involving surface trauma at the vessel wall where plaque may be dislodged, often produces enough localized injury that the vessel responds over time by cell proliferation and reocclusion. Not surprisingly, the occurrence or severity of restenosis is often related to the extent of vessel stretching involved in the angiographic procedure. Particularly where overstretching is 35% or more, restenosis occurs with high frequency and often with substantial severity, i.e., vascular occlusion.

In practicing the present invention, the stent is placed in its contracted state typically at the distal end of a catheter, either within the catheter lumen, or in a contracted state on a distal end balloon. The distal catheter end is then guided to the injury site, or the site of potential occlusion, and released from the catheter, e.g., by using a trip wire to release the stent into the site, if the stent is self-expanding, or by expanding the stent on a balloon by balloon inflation, until the stent contacts the vessel walls, in effect, implanting the stent into the tissue wall at the site.

Figure 5:
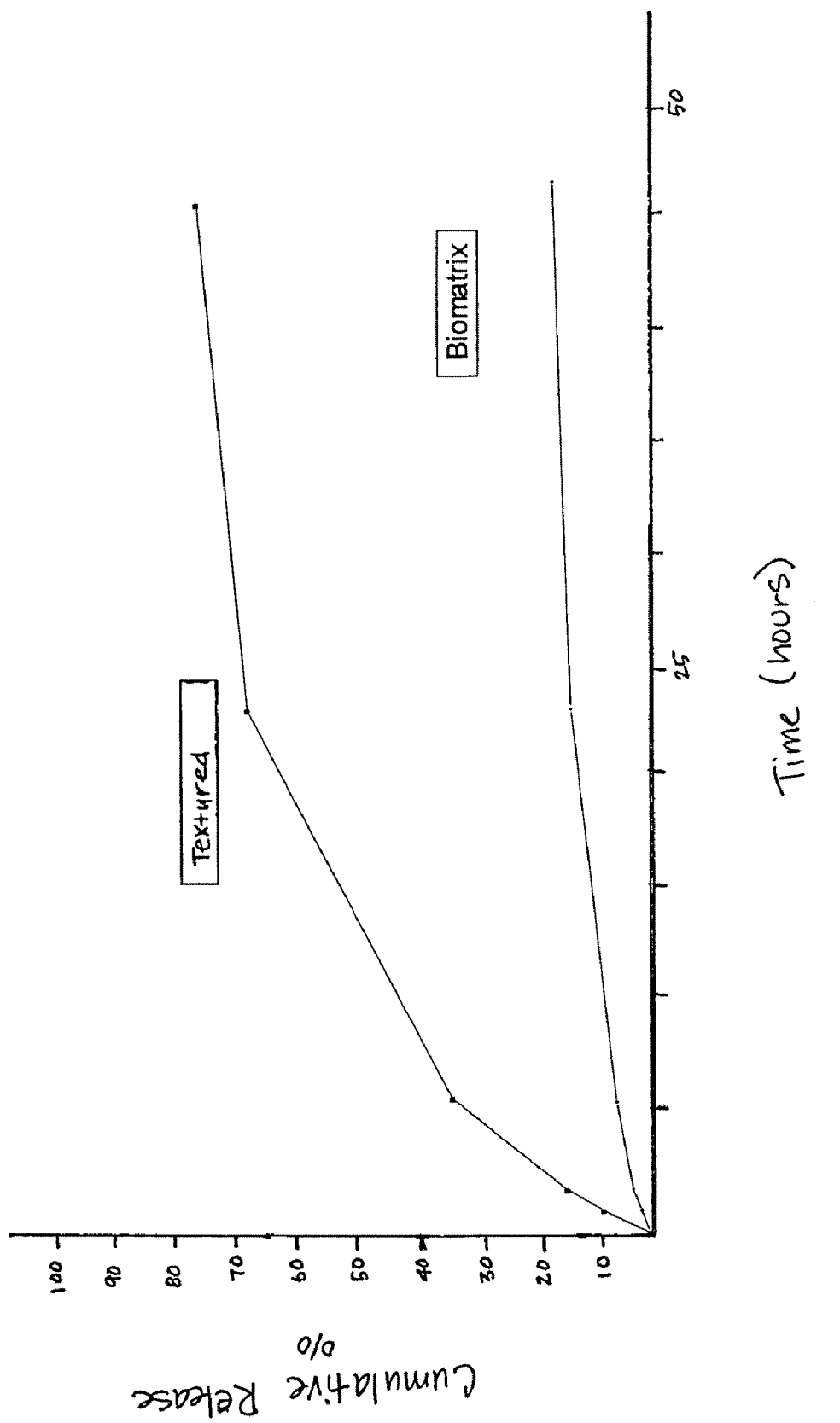
FIG. 5 is an elution profile of the drug Biolimus A9® from the present stent and the Biomatrix® II stent as measured by the percentage of the total amount of drug released over cumulative time in hours.

Once deployed at the site, the stent begins to release active compound into the cells lining the vascular site, to inhibit cellular proliferation. FIG. 5 shows Biolimus A9® release kinetics from two stents, one with the drug coated onto a textured surface and the other a Biomatrix® II stent with a polymer coating containing Biolimus A9®.

Figure 6:
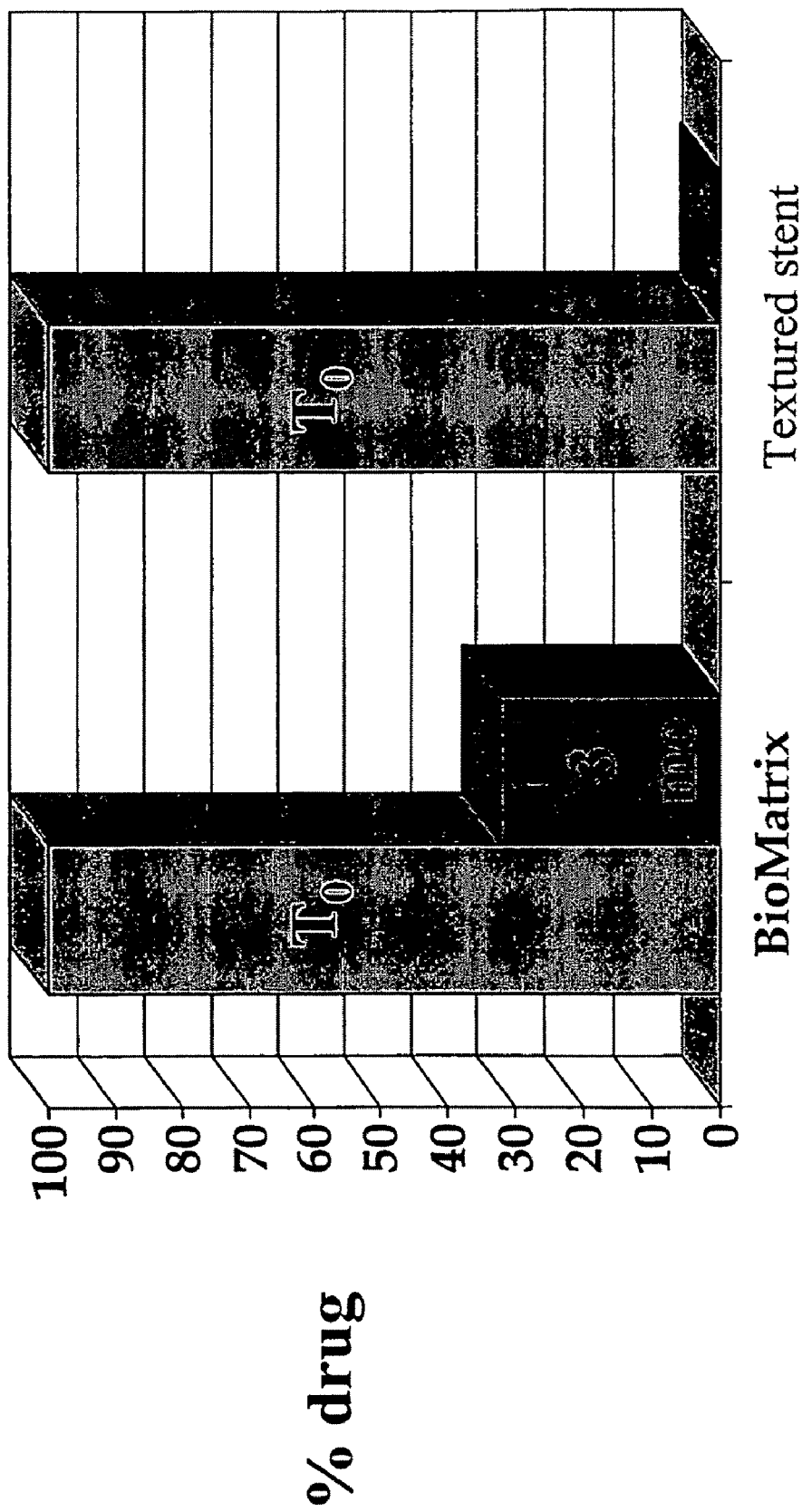
FIG. 6 is a graph showing the percentage of the drug Biolimus A9® released from the present stent and a Biomatrix® II in a porcine implant model at three and two months, respectively.

FIG. 6 shows the percentage of drug release of Biolimus A9® from a polymer coated and textured stent. As seen in the graph, after only two months, 100% of the Biolimus A9® was released from the textured stent. In contrast, after three months approximately 30% of the drug remained on the stent.

Figure 7:
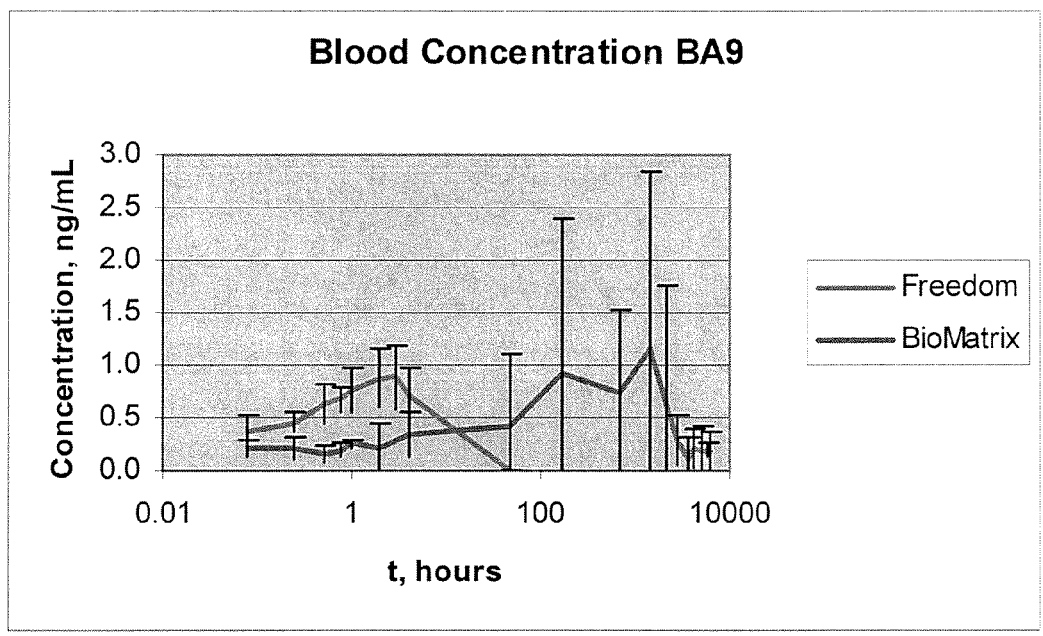
FIG. 7 is a graph showing the peak concentration in ng/mL of the drug Biolimus A9® in peripheral blood over time in hours as released from the present stent and a Biomatrix® II stent in a porcine implant model as measured by mass spectroscopy.

FIG. 7 shows the peak blood concentration of Biolimus A9® as measured by mass spectroscopy for each of the polymer coated Biomatrix® II and textured stent. As seen in the figure, the Biolimus A9® blood concentration peaks at about four hours with the textured stent. The peak blood concentration of Biolimus A9® with the polymer coated Biomatrix® II is at about two months.

FIGS. 9A-9F shows in cross-section, a vascular region having an implanted bare metal stent (FIGS. 9A-9B), a metal Biomatrix® II stent having a polymer coating of 225 µg PLA and 225 µg Biolimus A9® (FIGS. 9C-9D), and a textured stent with 225 µg Biolimus A9® (FIGS. 9E-9F), where the coated filaments are seen in cross section. The figure illustrates the release of anti-restenosis compound from each filament region into the surrounding vascular wall region. Over time, the smooth muscle cells forming the vascular wall begin to grow into and through the lattice or helical openings in the stent, ultimately forming a continuous inner cell layer that engulfs the stent on both sides. If the stent implantation has been successful, the extent of late vascular occlusion at the site will be less than 50%, that is, the cross-sectional diameter of flow channel remaining inside the vessel will be at least 50% of expanded stent diameter at time of implant.

Trials in a swine restenosis animal model as generally described by Schwartz et al. ("Restenosis After Balloon Angioplasty-A Practical Proliferative Model in Porcine Coronary Arteries", *Circulation* 82:(6) 2190-2200, December 1990.) demonstrate the ability of the stent of this invention to limit the extent of restenosis, and the advantages of the stent over currently proposed and tested stents. The studies are summarized in Example 2.

Briefly, the studies compare the extent of restenosis at 28 days following stent implantation, in bare metal stents, polymer-coated stents, and textured stents. FIGS. 9A-9F show that both the polymer coated and textured stent greatly reduced levels of restenosis. In general, the vessels with polymer drug-coated and textured stent treatment appeared to be well-healed with a well established endothelial layer, evidence of complete healing and vessel homeostasis at 28 days post implant.

The photographs show that the textured stent is at least equivalent to a stent with a drug eluting polymer coating.

The following examples illustrate various aspects of the making and using the stent invention herein. They are not intended to limit the scope of the invention.

EXAMPLE 1

In vitro Drug Release of Biolimus A9® from Stents

In vitro drug release was conducted for Biomatrix® II stents coated with a polymer containing Biolimus A9® and stents with abluminal microstructure including Biolimus A9® according to known methods in a PBS pH 7.4/Tween medium at 37° C. Sampling was periodically conducted and the total amount of Biolimus A9® was measured by HPLC. FIG. 5 illustrates drug release from the Biomatrix® II stent and the microstructure stent.

EXAMPLE 2

Animal Implant Tests

Textured stents with and without Biolimus A9® were implanted in out-bred juvenile swine. A balloon catheter was used to place the stent according to the standard porcine overstretch model with 10-20% overstretch. The juvenile swine were predilated prior to stent placement.

After 28 days, the animals were euthanized according to approved protocols, the heart and surrounding tissue was removed from the animals.

Figures 10A, 10B, 10C, 10D, 10E, 10F, 10G, 10H, 10I:
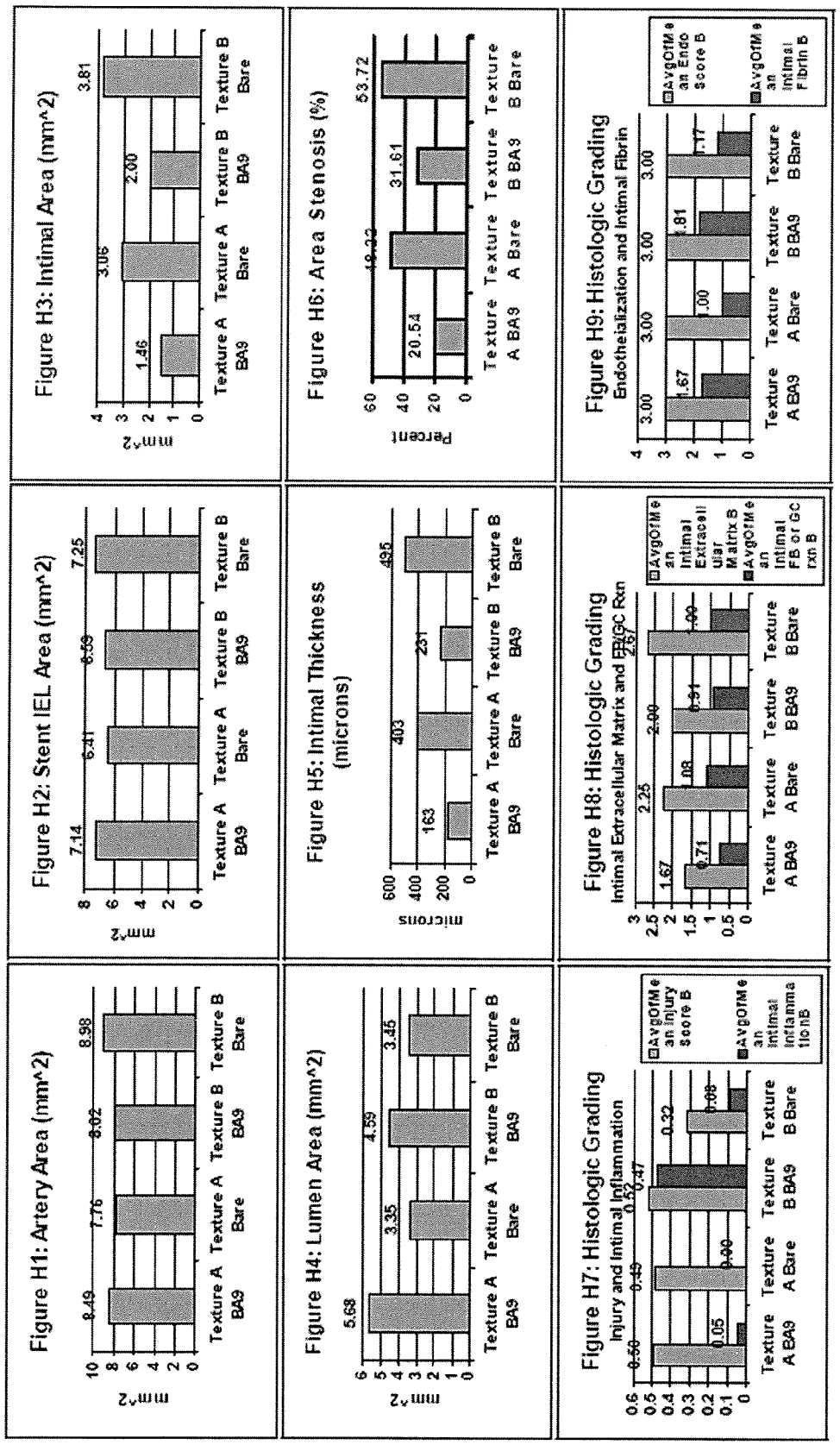

A microscope containing a digital camera was used to generate high resolution images of the vessel cross-sections which had been mounted to slides with the results shown in FIGS. 9A-9F. The images were subjected to histomorphometric analysis by the procedure as follows:

The stent and artery were dissected, and micro-tomed by a histologist. The samples were stained for various growth signals, cell proliferation, and other cellular debris. Histomorphometric measurements were made of:

The artery area in mm² (FIG. 10A), IEL (FIG. 10B), intimal area in mm² (FIG. 10C), lumen area in mm² (FIG. 10D), intimal thickness in microns (FIG. 10E), % area stenosis (FIG. 10F), histologic grading based on injury and inflammation (FIG. 10G), histologic grading based on intimal extracellular matrix and EB/GC reaction (FIG. 10H), histologic grading based on endothelialization and intimal fibrin (FIG. 10I), histologic grading based on medial inflammation, necrosis and fibrosis (FIG. 10J), and histologic grading based on adventitial inflammation and fibrosis (FIG. 10K).

The following table shows the results of the treatment effect at 28 days follow-up. The data in the tables below under column heading "Lumen Area mm²" report the results of morphometric analysis of stents and vessels removed from the pigs at 28 days follow-up (f/u):

TABLE 1

Histomorphometry results

| Stent | Arterial Area mm² | Lumen/Artery Ratio | Injury Score | Lumen Area mm² |
|---|---|---|---|---|
| Bare stent with textured ablation surface | 7.76 mm² | 1.08 | 0.57 | 3.35 ± 0.66 |
| Biomatrix stent with textured surface and 225 µg Biolimus A9 ® | 8.49 mm² | 1.08 | 0.50 | 5.68 ± 0.68 |

Figure 8:
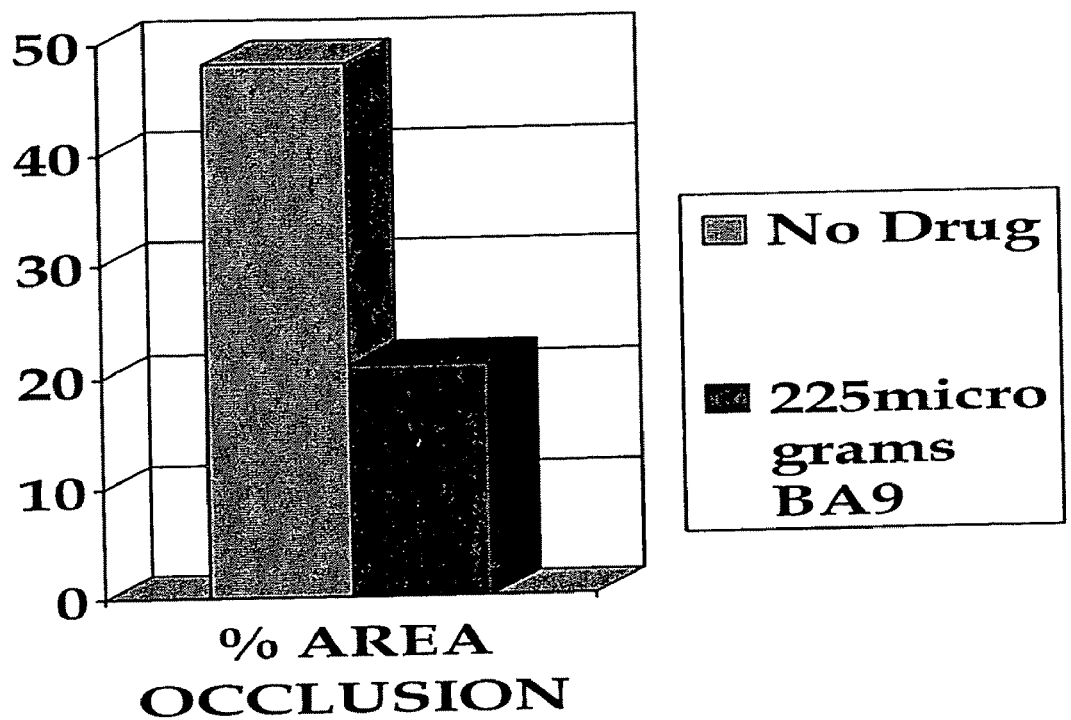
FIG. 8 is a graph showing the percentage of area occlusion for a stent having no drug and a stent having the Biolimus A9® drug.
Figure 9A:
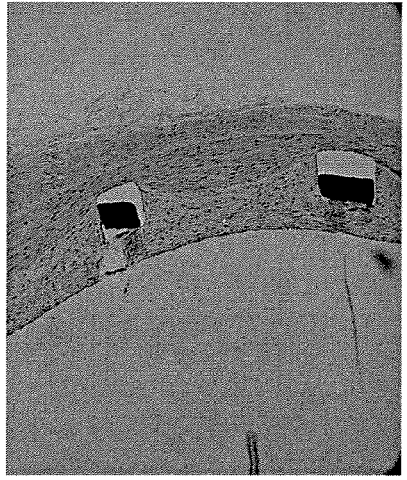
FIGS. 9A-9F are scanned images of histological sections of a vessel 28 days after implantation of a bare-metal stent (FIGS. 9A-9B), a metal-filament stent with a polymer coating containing Biolimus A9® (FIGS. 9C-9D), and metal-filament microstructure stent with a coating of Biolimus A9® (FIGS. 9E-9F)
Figure 9C:
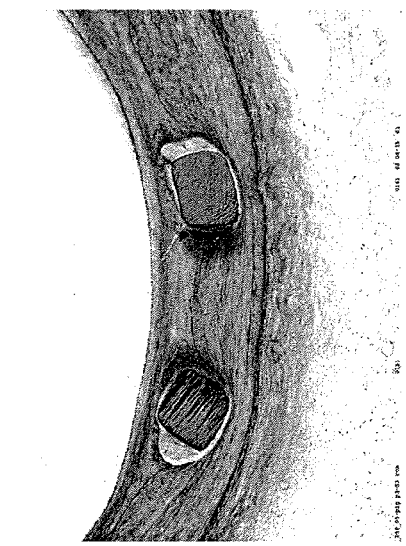
Figure 9E:
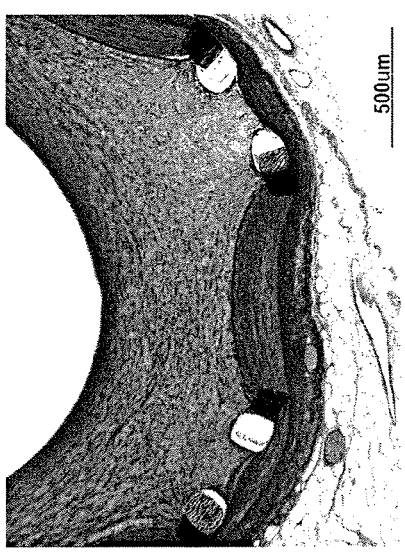
Figure 9B:
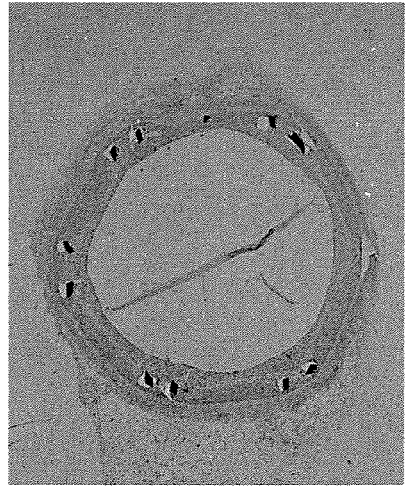
Figure 9D:
Figure 9F:
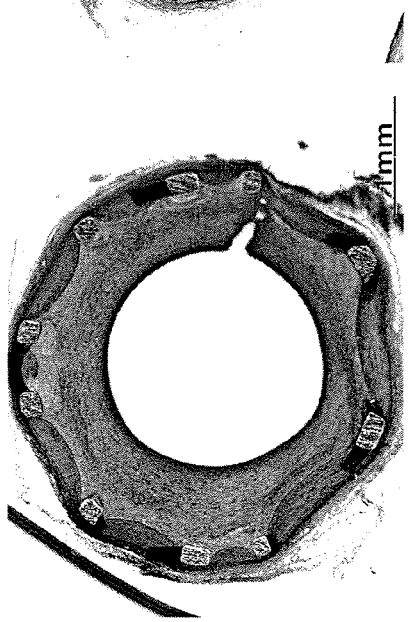

FIG. 8 shows the graph of the % area occlusion for each of the stent with textured surface and the stent with textured surface and pg Biolimus A9®.

The description of the invention is merely exemplary in nature and thus, variations that do not depart from the gist of the invention are intended to be within the scope of the invention. Such variations are not to be regarded as a departure from the spirit and scope of the invention.

It is claimed:

1. A method of producing a radially expandable, endovascular stent designed for placement at a site of vascular injury, for inhibiting restenosis at the site, comprising positioning the stent onto a mandrel covered with an exterior mask of hydrocarbon film; crimping the stent into the mask; ensuring that at least a portion of the stent that is not to be abraded is covered by the mask; texturing at least a portion of the stent; and applying a therapeutic agent to at least a portion of the abraded, roughened, or textured portion of the stent.

2. The method according to claim 1, wherein said applying a therapeutic agent comprises infusing the agent into a substratum formed in the abraded, roughened, or textured surface.

3. The method according to claim 1, further comprising removing said mask after said texturing.

4. The method according to claim 1, wherein said texturing comprises microblasting at least a portion of the stent.

5. The method according to claim 1, wherein said texturing comprises shot peening at least a portion of the stent.

6. The method according to claim 1, wherein said texturing comprises differentially compressing the stent.

7. The method according to claim 1, further comprising passivating at least a portion of the stent after said texturing.

8. The method according to claim 1, wherein said therapeutic agent comprises an anti-restenosis drug.

* * * * *